United States Patent [19]
de la Rama et al.

[11] Patent Number: 5,782,900
[45] Date of Patent: Jul. 21, 1998

[54] CATHETER SYSTEM HAVING SAFETY MEANS

[75] Inventors: Alan de la Rama, Cerritos; Weng-Kwen Raymond Chia, Irvine; Hosheng Tu, Tustin, all of Calif.

[73] Assignee: Irvine Biomedical, Inc., Irvine, Calif.

[21] Appl. No.: 880,837

[22] Filed: Jun. 23, 1997

[51] Int. Cl.$^6$ .................................................. A61N 1/05
[52] U.S. Cl. .......................... 607/122; 600/374; 606/41; 607/101; 607/104; 607/120
[58] Field of Search .......................... 600/373, 374, 600/377; 607/119, 120, 122, 96, 99, 101, 102, 104, 105, 113, 116; 606/41, 46, 49

[56] References Cited

U.S. PATENT DOCUMENTS

| | | |
|---|---|---|
| 4,832,048 | 5/1989 | Cohen ............................... 607/122 |
| 4,960,134 | 10/1990 | Webster, Jr. |
| 5,324,324 | 6/1994 | Vachon et al. ..................... 607/120 |
| 5,697,927 | 12/1997 | Imran et al. ....................... 606/41 |

Primary Examiner—Jeffrey R. Jastrzab

[57] ABSTRACT

A catheter system suitable for electrophysiology mapping and radiofrequency ablation of cardiac tissue comprises a catheter shaft having a distal end, a proximal handle, and at least a lumen extending therebetween, wherein a distal section of the shaft is either a fixed curve or deflectable; and safety anchoring means being provided to maintain the integrity of the catheter by holding the tip electrode in place. In one embodiment, the safety means is a tip electrode with safety anchoring pins. In another embodiment, the safety means is a tip electrode with extended flexible stem having open slots on said stem.

7 Claims, 6 Drawing Sheets

CATHETER SYSTEM HAVING SAFETY MEANS

FIELD OF THE INVENTION

The present invention generally relates to improved constructions for catheter system. More particularly, this invention relates to methods and apparatus for diagnosing and treating cardiac arrhythmias via a cardiovascular catheter system having safety means to maintain the integrity of the catheter system.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic region" or "accessory atrioventricular pathway" close to the inner surface of the chambers of a heart. The heart includes a number of normal pathways which are responsible for the propagation of electrical signals from upper to lower chamber necessary for performing normal function. The presence of arrhythmogenic region or accessory pathways can bypass or short circuit the normal pathways, potentially resulting in very rapid heart contractions, referred to here as tachycardias.

Cardiac mapping is used to locate aberrant electrical pathways and currents emanating within the heart. The aberrant pathways cause the contractions of the heart muscle to take on abnormal and life threatening dysrhythmias. Intracardiac mapping requires careful positioning of a plurality of catheters of multiple electrodes within the heart. For example, Webster, Jr. in U.S. Pat No. 4,960,134 shows the general use of a catheter. It is important for a catheter to move into and out of the heart chamber freely without any obstruction or potential complications of components disengagement from the catheter shaft.

Treatment of tachycardias may be accomplished by a variety of approaches, including drugs, surgery, implantable pace(makers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a clinician to be able to accurately steer the catheter to the region for ablation. Once at the region, it is important for a catheter to intimately contact the tissue to effectively control the emission of energy to ablate the tissue within the heart.

Regardless of the type of mapping means or ablation means used, the clinician is called upon to remotely move, rotate, push, pull, and manipulate the catheters in various ways. First, a catheter is inserted into a major vein or artery, usually in the neck or groin area. It is then guided into chambers of the heart by appropriate manipulation through the vein or artery. The distal section of a catheter must be manipulatable by a user from the proximal end of the catheter, so that the electrodes at the distal section can be positioned against the tissue at the desired location to assure that all aberrant electrical pathways are mapped and later ablated.

Development of prior catheters has focused upon the requirements of electrical continuity and interference problems. However, the mechanical and safety considerations have been overlooked. A conducting wire is soldered to the tip electrode or the band electrode. The electrode with a conducting wire is thereafter placed and secured onto the catheter shaft, mostly by gluing. The adhering force between a tip electrode and the catheter shaft is proportional to the contact surface area. It has been reported that the tip electrode might sometimes disengage from the distal section of the catheter shaft. The frequency of tip electrode disengagement becomes more often when a longer tip electrode is used for atrial flutter applications. In an atrial flutter procedure, a tip electrode of 8 mm length or longer is generally required. In this case, the contact area for gluing between the stem of electrode and the inner surface of the catheter shaft is not proportionally increased. The electrode is generally prone to separating from its main catheter shaft body because of inadequate contact area and subsequently gluing strength. The tip electrode might inadvertently be separated from the catheter shaft and left behind in a patient's heart or a circulation system. The prior development has overlooked the important need to provide a safe, intact catheter system having safety means in addition to the gluing force. It is the objective of this invention to provide needed safety means for the electrophysiology cardiovascular catheter system having a tip electrode.

SUMMARY OF THE INVENTION

It is an object of the present invention to provide an improved catheter system which can be used in mapping and ablating the arrhythmogenic region. It is another object of the present invention to provide safety means to the catheter system so that the integrity of the catheter is maintained throughout the clinical procedures.

In one embodiment, a catheter system of this invention comprises a catheter shaft having a distal section, a distal end, a proximal end, and at least one lumen extending therebetween; a handle attached to the proximal end of the shaft; a plurality of electrodes disposed at the distal section, wherein a tip electrode is secured at the distal end of the catheter; and a plurality of safety anchoring pins secured on the tip electrode for anchoring said electrode to the catheter shaft. The safety anchoring pins are to be secured into the matching holes on the catheter shaft, optionally with addition of adhesives or glues. By using the safety anchoring pins, the tip electrode is firmly secured on the catheter shaft. The safety anchoring pins may be made of the same material as the tip electrode. In an alternate embodiment, the safety anchoring pins are formed in non-circular shape, such as square, diamond or irregular shape to enhance anchoring effectiveness. The elevation of the safety anchoring pins can be about a fraction of millimeter up to 1 milliliter. The elevation at the proximal end of the anchoring pins may be lower than that at the distal end to facilitate easy insertion of the stem of a tip electrode into the catheter shaft during fabrication operations.

In another embodiment, a catheter system of this invention comprises a catheter shaft having a distal section, a distal end, a proximal end, and at least one lumen extending therebetween; a handle attached to the proximal end of the shaft; a plurality of electrodes disposed at the distal section, wherein a tip electrode is secured at the distal end of the catheter; and an extended stem of the tip electrode having at least one open slot in the axial direction on the stem being provided. In an alternate embodiment, the extended stem of the tip electrode is a flexible stem. The open slot on the stem is to provide adequate clearance for at least a conducting wire to enter from the adjacent band electrodes into the lumen. The extended flexible stem may consist of the material such as the braided metal mesh in a spiral-convoluted form. The length of the extended stem may be equal to or longer than the length of the tip electrode. In a preferred embodiment, the proximal end of the stem having at least one open slot in a catheter system extends proximally beyond the distal edge of the first band electrode.

The distal section of the catheter system of this invention can be either a fixed curve type or a deflectable curve type. In an exemplary embodiment, the means for deflecting the distal section of the steerable catheter comprises at least two pull wires along with a support wire. Said pull wires are attached to radially offset locations at the distal end of the deflectable section of the catheter shaft whereas at least a support wire radially inbetween the pull wires, and means at the proximal end of the shaft for selectively applying tension to the pull wires to cause deflection of the deflectable portion. In certain cases, the function of a support wire can be substituted by a spring coil which is stationary at its proximal end with respect to the shaft. The catheter system further comprises a steering mechanism at the handle, wherein said steering mechanism provides a plurality of deflectable curves on the tip section of the catheter assembly. The incorporation of the steering mechanism in a catheter is well known to those who are skilled in the art.

Usually in another embodiment for a steerable catheter of this invention, the distal section of the shaft may include at least three radially offset lumens, and wherein the two pull wires and one support wire are disposed in the central lumen of the catheter shaft over a proximal section thereof; the two pull wires disposed in the radially offset lumens over the distal section thereof, and the support wire disposed in the central lumen.

The means for selectively applying tension comprises a steering mechanism in the handle, and means for applying torque to the core wire comprises a rotatable ring or pushpull button disposed on the handle, the ring or button being coupled to the proximal end of the core wire. A variety of other tension applying mechanisms, such as joy sticks, may also be employed.

Signal conducting electrodes are placed on the distal section while their insulated conducting wires are passed through the shaft lumen to the connector secured at the proximal end of the handle. The main purpose of the conducting wires is to transmit the electric signal and to provide means for RF energy delivery. The safety anchoring pins and extended flexible stem on the tip electrode reinforce the gluing strength of the tip electrode.

In an alternate embodiment, a fluid source is positioned at one end of the catheter system for supplying a fluid flow through a lumen of said catheter system to the tip section which has a fluid vent opening. Therefore at ablation time, the tip section with a tip electrode is positioned against the tissues to be ablated. The fluid is continuously or intermittently supplied through the opening to cover and rinse the tissue contact site so that the impedance rise at the contact site is substantially reduced. The appropriate fluid flow rate for fluid irrigation is preferably in the range of 5 cc/min to 20 cc/min. By cooling off the electrode during RF energy delivery will result in optimal ablation efficiency.

A fluid conveying lumen is associated with the catheter system, and is preferably disposed within a separate lumen of the catheter system along the longitudinal axis thereof The lumen is adapted to communicate with a fluid supply source to convey fluid from the source and through the lumen to be discharged through the opening of the tip section and diffuse out of the tip section containing a tip electrode. The catheter system further comprises fluid being selected from the group of saline, heparin, antibiotics, chemotherapy and therapeutic fluids.

The invention also comprises a method and system for controlling the flow rate of fluid through the lumen to optimize the cooling effect of the energy delivering tip electrode. The control system preferably regulates the flow rate based on signals representative of the temperature of the catheter tip and/or tissue impedance.

A method for positioning a catheter system having safety means at its distal section within a heart chamber comprises percutaneously introducing the distal end of a catheter through an artery or vein to the heart chamber. Once the catheter tip is at the desired location, the handle at the proximal end is connected to the EKG monitor. And the electrical signal from the electrodes on the distal section can be transmitted to the exterior EKG monitor for cardiac mapping. Alternately, the radio frequency energy can be supplied to one or more of the electrodes on the distal section once an intimate contact with the tissue is achieved using the catheter of this invention.

The method and apparatus of the present invention have several significant safety advantages over known catheters. In particular, the safety anchoring pins on the tip electrode to match the receptacle holes on the catheter shaft and/or the extended flexible stem on the tip electrode maintains the integrity of the catheter system from potential complications of undesired components disengagement.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
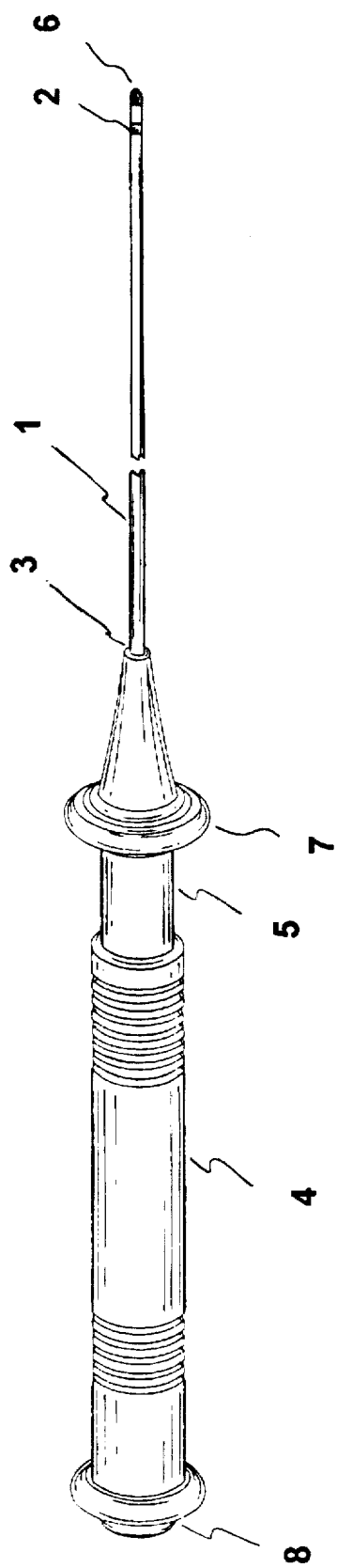
FIG. 1 is an overall view of the catheter system having safety means constructed in accordance with the principles of the present invention.

FIG. 1 shows a catheter system constructed in accordance with the principles of the present invention comprising: a catheter shaft 1 having a distal tip section 2, a distal end 6, a proximal end 3 and at least a lumen extending therebetween. A handle 4 is attached to the proximal end 3 of the catheter shaft 1. The tip section 2 may be a fixed curve type or deflectable by employing a steering mechanism 5 at the handle 4. A push-pull plunger 7 is employed to deflect the tip section 2 of the catheter shaft 1. A connector 8 is secured at the proximal end of the handle 4. At least one electrode available for electrophysiology use is disposed on the tip section 2.

Figure 2:
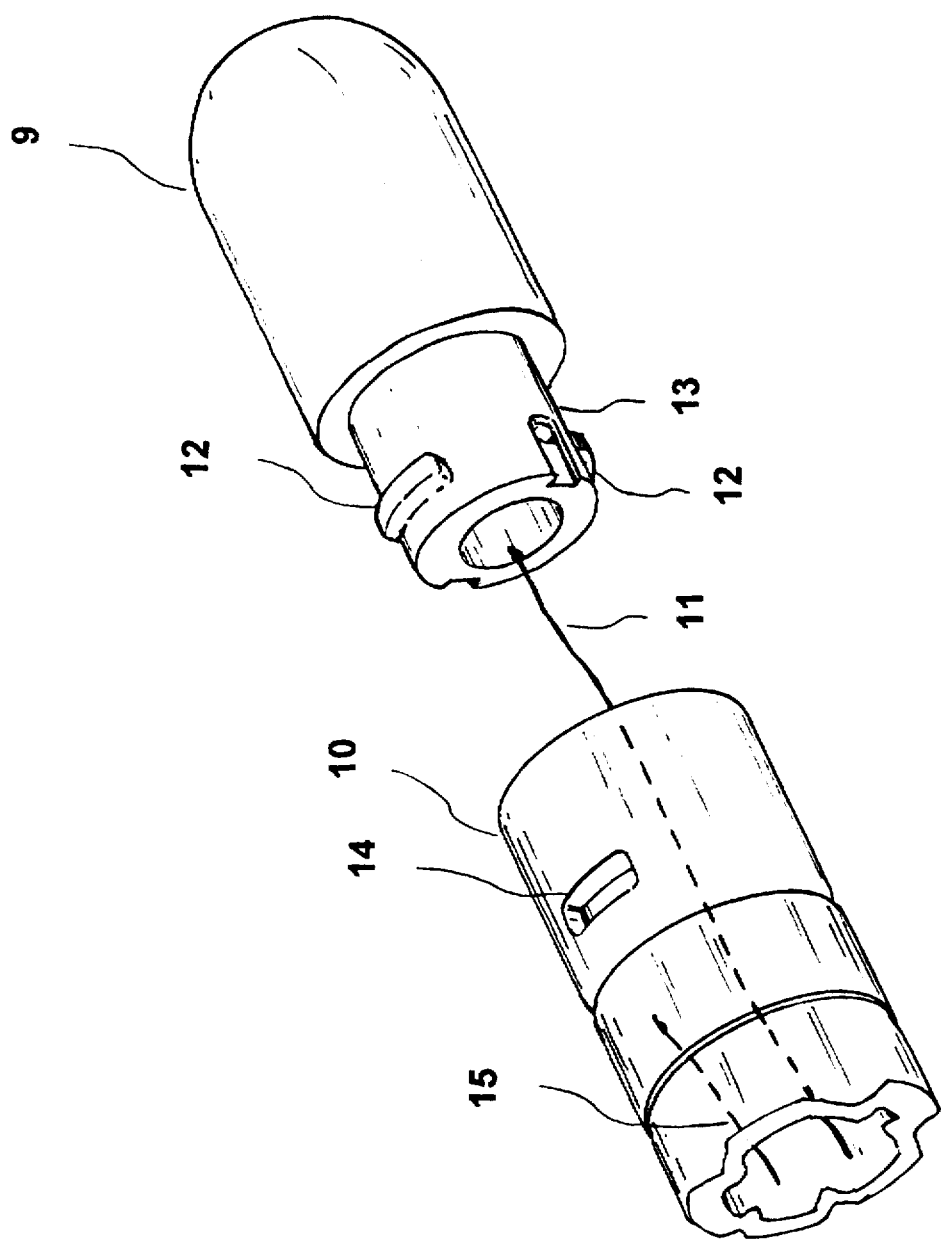
FIG. 2 is a perspective view of the distal section of the catheter system with safety anchoring pins as safety means.

FIG. 2 shows a perspective view of the distal section of a catheter system with safety anchoring pins as safety means of FIG. 1. The tip electrode 9 which has a conducting wire 11 soldered onto it is attached to the catheter shaft 10 using either epoxy or glue. A plurality of safety anchoring pins 12 is secured on the stem 13 of the tip electrode 9. A plurality of matching holes 14 on the catheter shaft 10 is provided. When securing the tip electrode 9 to the tip section 2 of the catheter system, the anchoring pins 12 fit tightly the matching holes 14. Adhesive and/or glue may be added when securing the anchoring pins 12 into the holes 14. By incorporating said safety means, the tip electrode 9 is secured onto the tip section of the catheter system.

Figure 3:
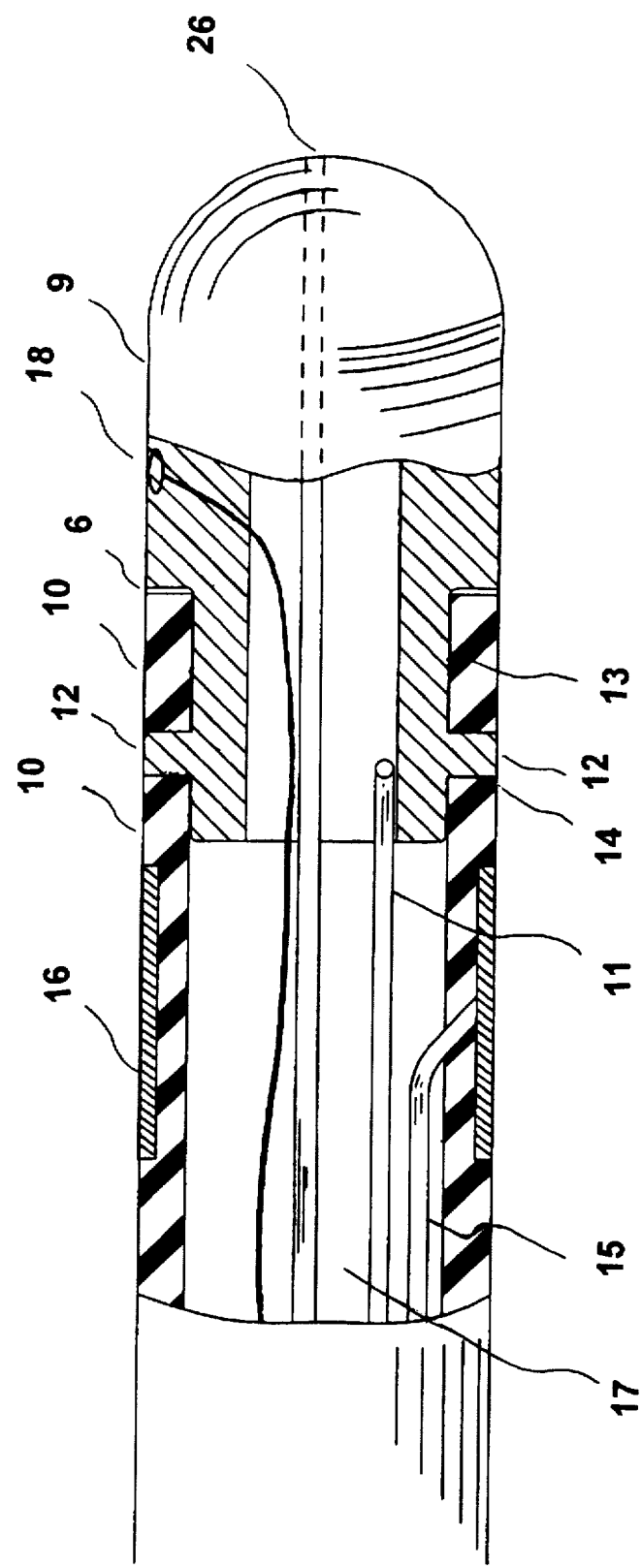
FIG. 3 is a close-up view of the distal section of the catheter system of FIG. 2.

FIG. 3 shows the cross-sectional view of the tip section of FIG. 2. During catheter fabrication, a tip electrode 9 with safety anchoring pins 12 on the stem 13 is inserted into the catheter shaft 10 of the catheter system. The anchoring pins 12 fit tightly into the matching holes 14 of the catheter shaft 10. A conducting wire 11 from the tip electrode 9 passed through the lumen 17 of the catheter shaft 10 and is secured to the connector 8 at the proximal end of the handle 4. Similarly, another conducting wire 15 from the band electrode 16 passes through the lumen 17 and is secured to the connector 8 at the proximal end of the handle 4. In an alternate embodiment, a temperature sensor 18 with a transmission means is secured at the surface of the tip electrode 9 where the tip electrode contacts the tissue during ablation procedure. The catheter system further comprises means for supplying fluid to the proximal end through the at least one lumen 17 to the distal tip section 2 of the catheter system, and adapted to be disposed out of the tip electrode 9, wherein the tip electrode has an opening 26 for fluid disposal.

Figure 4:
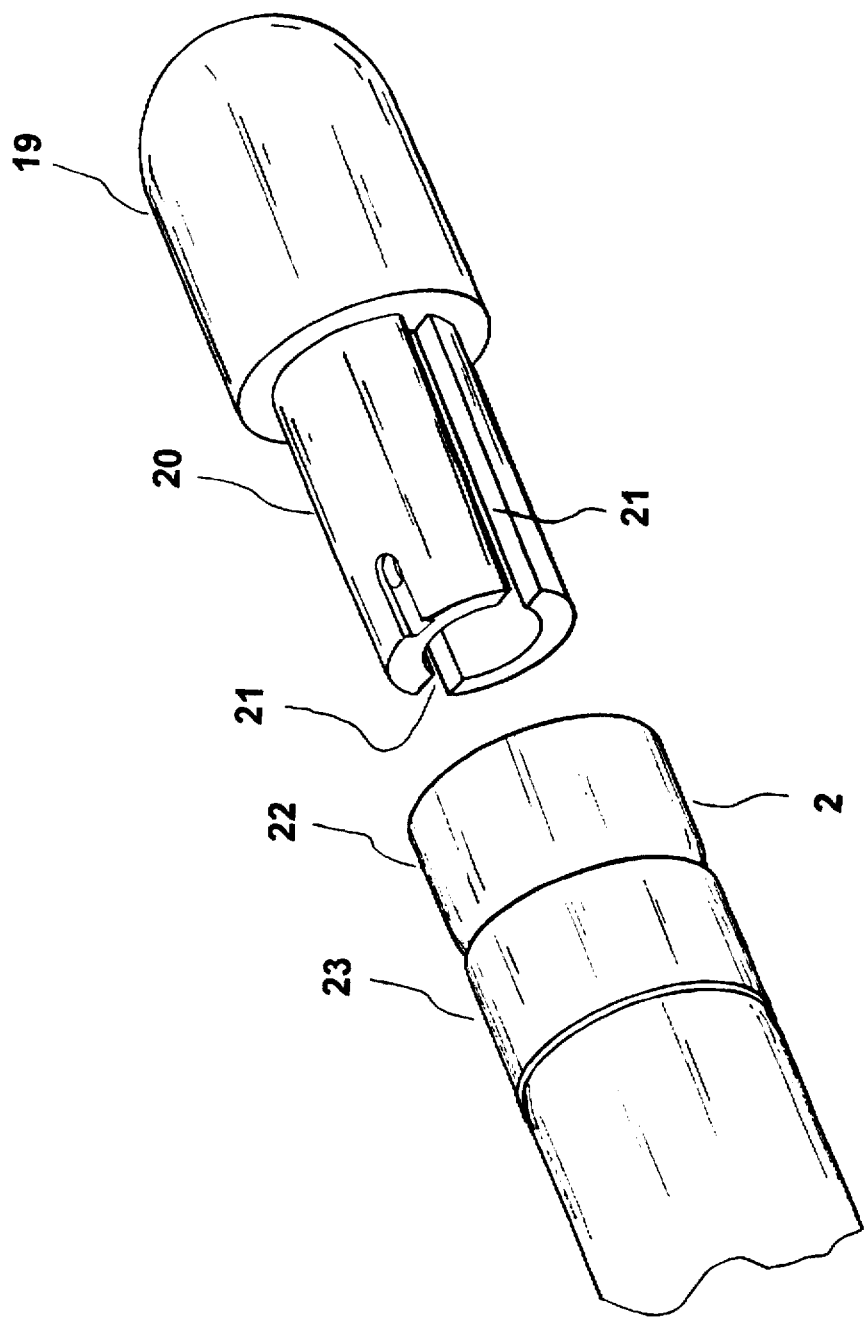
FIG. 4 is a perspective view of the distal section of the catheter system with an extended flexible stem as safety means.

FIG. 4 shows a perspective view of the distal section of a catheter system with an extended flexible stem as safety means. The tip electrode 19 which has a long stem 20 and has at least one open slot 21 on the stem 20 is to be fitted into the catheter shaft 22 of the catheter system. At least a band electrode 23 is secured at the distal tip section 2 of the catheter system. A conducting wire from the band electrode 23 passes through the catheter shaft 22 through a small opening on the catheter shaft and enters into the lumen 17 and is thereafter secured to the connector 8 at the proximal end of the handle 4. When inserting the tip electrode 19 into the catheter shaft 22, The open slot 21 of the stem 20 by-passes the conducting wire entering from the band electrode 23. Therefore, a band electrode can be located very close to the tip electrode without concerning the obstruction of the long stem extending from the tip electrode. The length of the stem can therefore be as long as one wishes.

Figure 5:
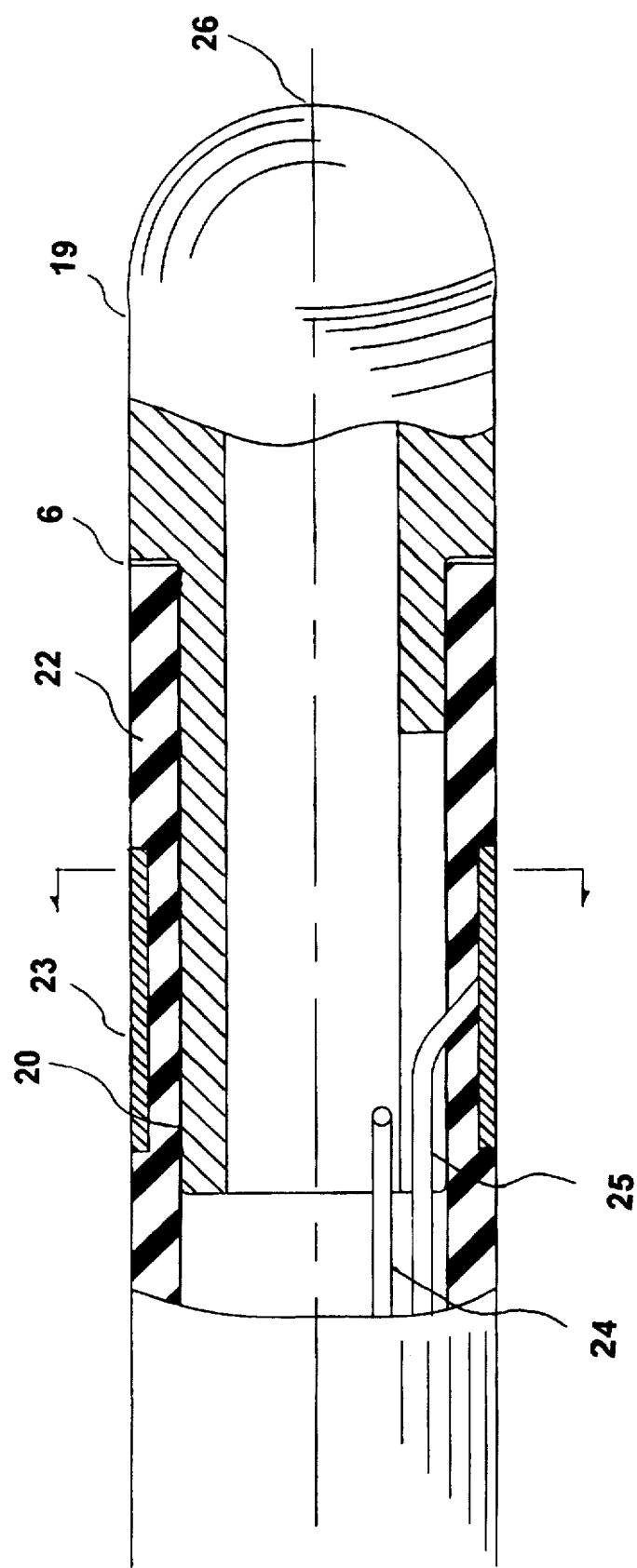
FIG. 5 is a close-up view of the distal section of the catheter system of FIG. 4.

FIG. 5 shows a close-up view of the distal section of the catheter system of FIG. 4.

Figure 6:
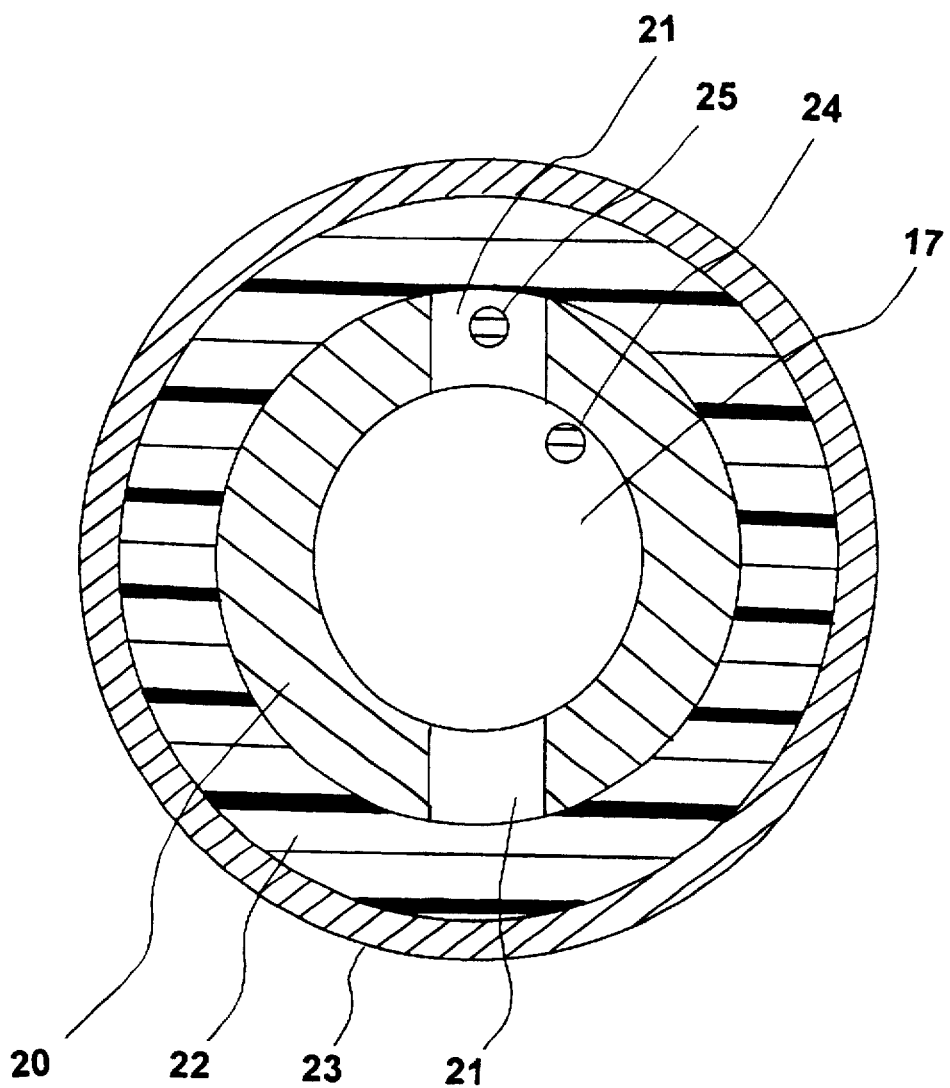
FIG. 6 is a cross-sectional view of the distal section of the catheter system of FIG. 5.

During a catheter fabrication process, a tip electrode 19 with a long stem 20 is attached to the catheter shaft 22 using either epoxy or glue type adhesive. A conducting wire 24 for the tip electrode 19 is used for EKG signal monitoring and for RF energy transmission. At least another conducting wire 25 for the band electrode 23 is used for EKG signal monitoring. FIG. 6 shows a cross-sectional view of the distal section of the catheter system of FIG. 5. The band electrode 23 overlays on the top of the catheter shaft 22. The stem 20 of the tip electrode 19 lies tightly underneath the catheter shaft 22. The conducting wire 25 from the band electrode 23 stays without any obstruction in the space provided by the open slot 21 of the stem 20. At least another open slot 21 is provided at the opposite side of the stem. The stem can be made of a flexible material. This flexible stem is especially useful in the distal tip section of a deflectable catheter.

In another embodiment, the steerable catheter of the present invention comprises a handle and a catheter shaft, wherein a tip electrode and at least one band electrode are disposed at the distal section of the catheter shaft. The steerable catheter has a push-pull plunger as a steering mechanism to deflect the tip of the catheter to a desired curve type.

The material of electrodes may be selected from the group of platinum, iridium, silver, gold or stainless steel. The spacing between the electrodes is in the range of 1 mm to 10 mm, preferably 2 to 5 mm. The length of the stem is in the range of 2 mm to 20 mm, preferably 2 to 10 mm.

From the foregoing, it should now be appreciated that an improved catheter system has been disclosed herein comprised of safety means to render a catheter less prone to disintegration. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
   (a) a catheter shaft having a distal section, a distal end, a proximal end, and at least one lumen extending therebetween;
   (b) a handle attached to the proximal end of the catheter shaft;
   (c) a plurality of electrodes disposed at the distal section, wherein a tip electrode is secured at the distal end of the catheter; and wherein a conducting wire is secured to each electrode;
   (d) a plurality of safety anchoring pins secured on the tip electrode for anchoring the said electrode to the catheter shaft; and
   (e) a plurality of matching holes being provided on the catheter shaft for receiving the anchoring pins.

2. The catheter system as in claim 1, further comprising the safety anchoring pins being formed in non-circular shape to enhance anchoring effectiveness.

3. The catheter system as in claim 1, further comprising the elevation of the safety anchoring pins being less than one millimeter.

4. The catheter system as in claim 1, further comprising a steering mechanism at the handle for the catheter system.

5. The catheter system as in claim 4, wherein said steering mechanism provides a plurality of deflectable curves on the tip section of the catheter assembly.

6. The catheter system as in claim 1, further comprising means for supplying fluid to the proximal end through the at least one lumen to the distal tip section of the catheter system, and adapted to be disposed out of the tip electrode, wherein the tip electrode has an opening for fluid disposal.

7. The catheter system as in claim 6, further comprising fluid being selected from the group of saline, heparin, antibiotics, chemotherapy and therapeutic fluids.

* * * * *